(12) United States Patent
Puskas

(10) Patent No.: US 8,580,917 B2
(45) Date of Patent: *Nov. 12, 2013

(54) METHOD OF PURIFYING BLOCK COPOLYMERS

(71) Applicant: The University of Akron, Akron, OH (US)

(72) Inventor: Judit E Puskas, Akron, OH (US)

(73) Assignee: The University of Akron, Akron, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/709,410

(22) Filed: Dec. 10, 2012

(65) Prior Publication Data

US 2013/0102711 A1 Apr. 25, 2013

Related U.S. Application Data

(63) Continuation of application No. 12/300,348, filed as application No. PCT/US2007/011831 on May 17, 2007, now Pat. No. 8,383,764.

(60) Provisional application No. 60/801,032, filed on May 17, 2006.

(51) Int. Cl.
*C08F 6/00* (2006.01)

(52) U.S. Cl.
USPC .......... 528/493; 528/480; 528/491; 528/495; 528/502 R; 528/502 A; 210/705; 210/712; 210/723; 210/725; 210/726; 210/727; 210/728; 210/729; 521/40; 521/40.5; 521/41

(58) Field of Classification Search
USPC .......... 521/40, 40.5, 41, 46, 47, 48; 528/480, 528/489, 491, 493, 494, 495, 496, 502 R, 528/502 A, 502 C, 503; 525/68, 95, 98, 241, 525/244, 314, 315, 316; 523/346, 347; 210/705, 712, 723, 725, 726, 727, 728, 210/729

See application file for complete search history.

(56) References Cited

U.S. PATENT DOCUMENTS

| | | | |
|---|---|---|---|
| 4,946,899 | A | 8/1990 | Kennedy et al. |
| RE34,640 | E | 6/1994 | Kennedy et al. |
| 5,395,855 | A | 3/1995 | Stanek et al. |
| 5,428,111 | A | 6/1995 | Faust et al. |
| 5,458,796 | A | 10/1995 | Storey et al. |
| 5,630,844 | A | 5/1997 | Dogan et al. |
| 5,721,331 | A | 2/1998 | Shachi et al. |
| 6,102,939 | A | 8/2000 | Pinchuk |
| 6,156,859 | A | 12/2000 | Langstein et al. |
| 6,197,240 | B1 | 3/2001 | Pinchuk |
| 6,741,331 | B2 | 5/2004 | Boonman et al. |
| 6,747,098 | B2 | 6/2004 | Puskas et al. |
| 2006/0013867 | A1 | 1/2006 | Richard et al. |
| 2010/0256305 | A1 | 10/2010 | Kaszas |

FOREIGN PATENT DOCUMENTS

WO        WO 02/32982        4/2002

*Primary Examiner* — Frances Tischler
(74) *Attorney, Agent, or Firm* — REnner Kenner Greive Bobak Taylor WEber

(57) ABSTRACT

The invention relates to block polymers, for example, arborescent copolymer compounds, and to methods of making and purifying such compounds. In one embodiment, the invention relates to arborescent polymer compounds that contain one or more styrene polymeric blocks in combination with one or more isobutylene polymeric blocks. In another embodiment, the invention relates to methods for purifying arborescent polymer compounds that contain at least one styrene polymeric block in combination with at least one isobutylene polymeric block.

60 Claims, No Drawings

US 8,580,917 B2

METHOD OF PURIFYING BLOCK COPOLYMERS

CROSS REFERENCE TO RELATED APPLICATION

This application is a continuation application of U.S. patent application Ser. No. 12/300,348, filed Jan. 14, 2009, which is a 371 national phase application of International PCT Application No. PCT/US2007/011831, filed May 17, 2007, abandoned, which claims the benefit of U.S. Provisional Application No. 60/801,032, filed May 17, 2006, abandoned, the entirety of all of these applications being incorporated herein by reference.

FIELD OF THE INVENTION

The invention relates to block polymers, for example, arborescent copolymer compounds, and to methods of making and purifying such compounds. In one embodiment, the invention relates to arborescent polymer compounds that contain one or more styrene polymeric blocks in combination with one or more isobutylene polymeric blocks. In another embodiment, the invention relates to methods for purifying arborescent polymer compounds that contain at least one styrene polymeric block in combination with at least one isobutylene polymeric block.

BACKGROUND OF THE INVENTION

Polymeric materials exhibiting both thermoplastic as well as elastomeric characteristics have a variety of unique properties that make them valuable articles of commerce. Such thermoplastic elastomers include block copolymers having the general structure of ABA (linear triblock), $A(BA)_n$ (linear alternating block), or $(AB)_n$-X (radial block) where A is a thermoplastic, glassy block with a high glass transition temperature, B is an elastomeric block, n is a positive whole number, and X is the initiator core or residue.

Thermoplastic elastomers can behave like vulcanized rubbers at room temperature and like thermoplastic polymers at higher temperatures. Thus, the materials can be melt extruded like plastics, while retaining their beneficial rubbery or elastic features upon cooling. This ability is not only advantageous during polymer processing, but actually allows for reprocessing as well. Furthermore, not only are such products fundamentally elastomeric but they exhibit physical behavior similar to elastomers that have been reinforced with reinforcing agents. In other words, the products behave substantially in the same manner as vulcanized rubbers, but without the need to subject them to vulcanization, which is often impractical because of the nature of the product being produced, for example, adhesives, coatings, elastic threads, biological implants, or medical device coatings.

Polymers having such dual nature have been known for some time but their application in biomedical and pharmaceutical fields may have been hindered due to the time, difficulty, and/or expense associated with purifying such polymers for biomedical and pharmaceutical applications. Accordingly, there is a need in the art for improved methods of polymer synthesis and/or purification as it relates to thermoplastic elastomers.

SUMMARY OF THE INVENTION

The invention relates to block polymers, for example, arborescent copolymer compounds, and to methods of making and purifying such compounds. In one embodiment, the invention relates to arborescent polymer compounds that contain one or more styrene polymeric blocks in combination with one or more isobutylene polymeric blocks. In another embodiment, the invention relates to methods for purifying arborescent polymer compounds that contain at least one styrene polymeric block in combination with at least one isobutylene polymeric block.

In one embodiment, the present invention relates to a method for purifying a block polymer comprising the steps of: (a) dissolving the block polymer in a first solvent system to provide a first solution, wherein the first solvent system comprises one or more solvents, and the solvent system is capable of dissolving a polyisobutylene-based block polymer; (b) combining the first solution with a second solvent system, wherein the second solvent system comprises one or more solvents, and the solvent system dissolves a polystyrene-based end block of the block polymer to a greater extent than it dissolves a polyisobutylene-based block of the block polymer, to provide a precipitated block polymer in a mother liquor; and (c) separating the precipitated block polymer from the mother liquor to provide a purified block polymer.

In one embodiment, the above method further comprises the steps of: (d) adding acetone to the purified block polymer to provide a mixture of the purified block polymer and acetone; (e) adding a third solvent system to the mixture of the purified block polymer and acetone, wherein the third solvent system is a non-solvent with respect to at least two types of blocks of the purified block polymer, to provide a mixture of the purified block polymer and the mixture of solvents; and (f) separating the purified block polymer from the mixture of solvents to provide a further purified block polymer.

In another embodiment, the present invention relates to a method for purifying a block polymer comprising the steps of: (i) dissolving the block polymer in a first solvent system to provide a first solution, wherein the first solvent system comprises one or more solvents, and the solvent system is capable of dissolving a polyisobutylene-based polymer; (ii) combining the first solution with a second solvent system, wherein the second solvent system comprises one or more solvents, and the solvent system dissolves a polystyrene-based end block of the block polymer to a greater extent than it dissolves a polyisobutylene-based block of the block polymer, to provide a precipitated block polymer in a mother liquor; (iii) separating the precipitated block polymer from the mother liquor to provide a purified block polymer; (iv) adding acetone to the purified block polymer to provide a mixture of the purified block polymer and acetone; (v) adding a third solvent system to the mixture of the purified block polymer and acetone, wherein the third solvent system is a non-solvent with respect to at least two types of blocks of the purified block polymer, to provide a mixture of the purified block polymer and the mixture of solvents; and (vi) separating the purified block polymer from the mixture of solvents to provide a further purified block polymer.

In still another embodiment, the present invention relates to a method for purifying a block polymer comprising the steps of: (A) dissolving about 1 part by weight of the block polymer in about 10-30 parts by weight of a first solvent system to provide a first solution, wherein the first solvent system comprises one or more solvents, and the solvent system is capable of dissolving a polyisobutylene-based polymer; (B) combining the first solution with about 5 to about 10 volumes of a second solvent system, with respect to the volume of the first solution, wherein the second solvent system comprises one or more solvents, and the solvent system dissolves a polystyrene-based end block of the block polymer to a greater extent than it dissolves the internal polyisobutylene-based blocks of the block polymer, to provide a precipitated block polymer in a mother liquor; (C) separating the precipitated block polymer from the mother liquor to provide a purified block polymer; (D) adding about 5 to about 10 volumes of acetone, with respect to the volume of the first solution, to the purified block polymer to provide a mixture of the purified block polymer and acetone; (E) adding about 1 to about 5 volumes, with respect to the volume of the first solution, of 2-propanol to the mixture of the purified block polymer and acetone, to provide a mixture of the purified block polymer and the mixture of solvents; optionally followed by adding an additional 1 to about 15 volumes of 2-propanol; and (F) separating the purified block polymer from the mixture of solvents to provide a further purified block polymer.

DETAILED DESCRIPTION OF THE INVENTION

The invention relates to block polymers, for example, arborescent copolymer compounds, and to methods of making and purifying such compounds. In one embodiment, the invention relates to arborescent polymer compounds that contain one or more styrene polymeric blocks in combination with one or more isobutylene polymeric blocks. In another embodiment, the invention relates to methods for purifying arborescent polymer compounds that contain at least one styrene polymeric block in combination with at least one isobutylene polymeric block.

In one embodiment, the present invention relates to a method for purifying a block polymer comprising: (a) dissolving the block polymer in a first solvent system to provide a first solution, wherein the first solvent system comprises one or more solvents, and the solvent system is capable of dissolving a polyisobutylene-based block polymer; (b) combining the first solution with a second solvent system, wherein the second solvent system comprises one or more solvents, and the solvent system dissolves a polystyrene-based end block of the block polymer to a greater extent than it dissolves a polyisobutylene-based block of the block polymer, to provide a precipitated block polymer in a mother liquor; and (c) separating the precipitated block polymer from the mother liquor to provide a purified block polymer.

In one embodiment, the present invention relates to block polymers (e.g., arborescent copolymer compounds), and to methods of making and purifying such compounds. The phase inversion purification described herein can be used to purify a wide variety of block polymers, such as polyisobutylene-based thermoplastic elastomers. In one instance, various examples of polymers that can be purified using the phase inversion purification described herein include, but are not limited to, the block polymers and thermoplastic elastomers disclosed in U.S. Pat. Nos. 4,946,899; 5,395,855; 5,428,111; 5,458,796; 5,630,844; 5,721,331; 6,741,331; 6,102,939; 6,156,859; 6,197,240; 6,747,098; and RE34,640, the disclosure of which are hereby incorporated herein in their entireties. In another instance, other examples of polymers that can be purified using a method in accordance with the present invention include, but are not limited to, the polymer and/or elastomer compounds disclosed in International Patent Application Publication No. WO 02/32982, the disclosure of which is hereby incorporated herein in its entirety. In still another instance, the present invention is used to purify polymers from those disclosed in the above patents where such polymers are suitable for biomedical applications.

In another embodiment, polymers according to those detailed in U.S. Provisional Patent Application No. 60/841,757, filed Sep. 1, 2006, and entitled "Arborescent Polymers and Process for Making Same." The above-identified provisional patent application is hereby incorporated by reference in its entirety.

Based on the above-identified United States Provisional Patent Application, additional polymers that can be purified via the present invention further include arborescent polymers formed from at least one inimer and at least one isoolefin that have been end-functionalized with a polymer or copolymer having a low glass transition temperature ($T_g$). In one embodiment, polymers for purification by the present invention can also include arborescent polymers formed from at least one inimer and at least one isoolefin that have been end-functionalized with less than about 5 weight percent end blocks derived from a polymer or copolymer having a high glass transition temperature ($T_g$). In still another embodiment, polymers for purification by the present invention can also include arborescent polymers formed from at least one inimer and at least one isoolefin that have been end-functionalized, where such polymers have a saturated core and one or more unsaturated end-functionalized portions.

In still another embodiment, polymers for purification by the present invention can also include arborescent polymers formed from at least one inimer and at least one isoolefin that have been end-functionalized with about 0.5 to about 50 weight percent end blocks derived from a polymer or copolymer having a low $T_g$. In another instance, polymers according to this embodiment, have from about 1 to about 40 weight percent end-blocks, or about 2 to about 30 weight percent end blocks, or about 3 to about 20 weight percent end blocks, or even from about 1 to about 25 weight percent end blocks. Here, as well as elsewhere in the specification and claims, individual range limits may be combined.

In yet another embodiment, polymers for purification by the present invention can also include arborescent polymers formed from at least one inimer and at least one isoolefin that have been end-functionalized with about 0.5 to about 5 weight percent end blocks derived from a polymer or copolymer having a high glass transition temperature ($T_g$). In another instance, polymers according to this embodiment, have from about 1 to about 4 weight percent end blocks, or even from about 1.5 to about 3.5 weight percent end blocks. In another instance, polymers according to this embodiment, are end-functionalized with styrene or a styrene derivative having a high glass transition temperature.

With regard to these polymers, a polymer or copolymer having a low glass transition temperature is defined to be a polymer or copolymer having a glass transition temperature of less than about 40° C. or less than about 35° C., or less than about 30° C., or even less than about 25° C. It should be noted that the previously stated ranges are intended to encompass any polymers and/or copolymers that have a glass transition temperature that falls below one of the previously stated thresholds.

Conversely, a polymer or copolymer having a high glass transition temperature is defined to be a polymer or copolymer having a glass transition temperature of more than about 40° C., or more than about 45° C., or more than about 50° C., or more even more than about 100° C. It should be noted that the previously stated ranges are intended to encompass any polymers and/or copolymers that have a glass transition temperature that falls above one of the previously stated thresholds.

In still another embodiment, polymers for purification by the present invention can also include arborescent polymers formed from at least one inimer and at least one isoolefin that have been end-functionalized with a low $T_g$ homo or copolymer that contains isoprene or any other cationically polymerizable monomer. In yet another embodiment, polymers for purification by the present invention can also include arborescent polymers that that have been end-functionalized and further include at least one filler, where such polymers have been formed from at least one inimer and at least one isoolefin. An exemplary reaction scheme for producing polymers according to this embodiment is shown below where each F represents one or more functional end blocks according to the present invention that preferentially interact with one more filler particles.

least one isoolefin is end-functionalized with a polymer or copolymer as is described above.

Formula (I) below details the nature of suitable inimer compounds that can be used in conjunction with at least one isoolefin to form a polymer in accordance with the disclosure contained in U.S. Provisional Patent Application No. 60/841,757. In Formula (I) A represents the polymerizable portion of the inimer compound, while B represents the initiator portion of the inimer compound.

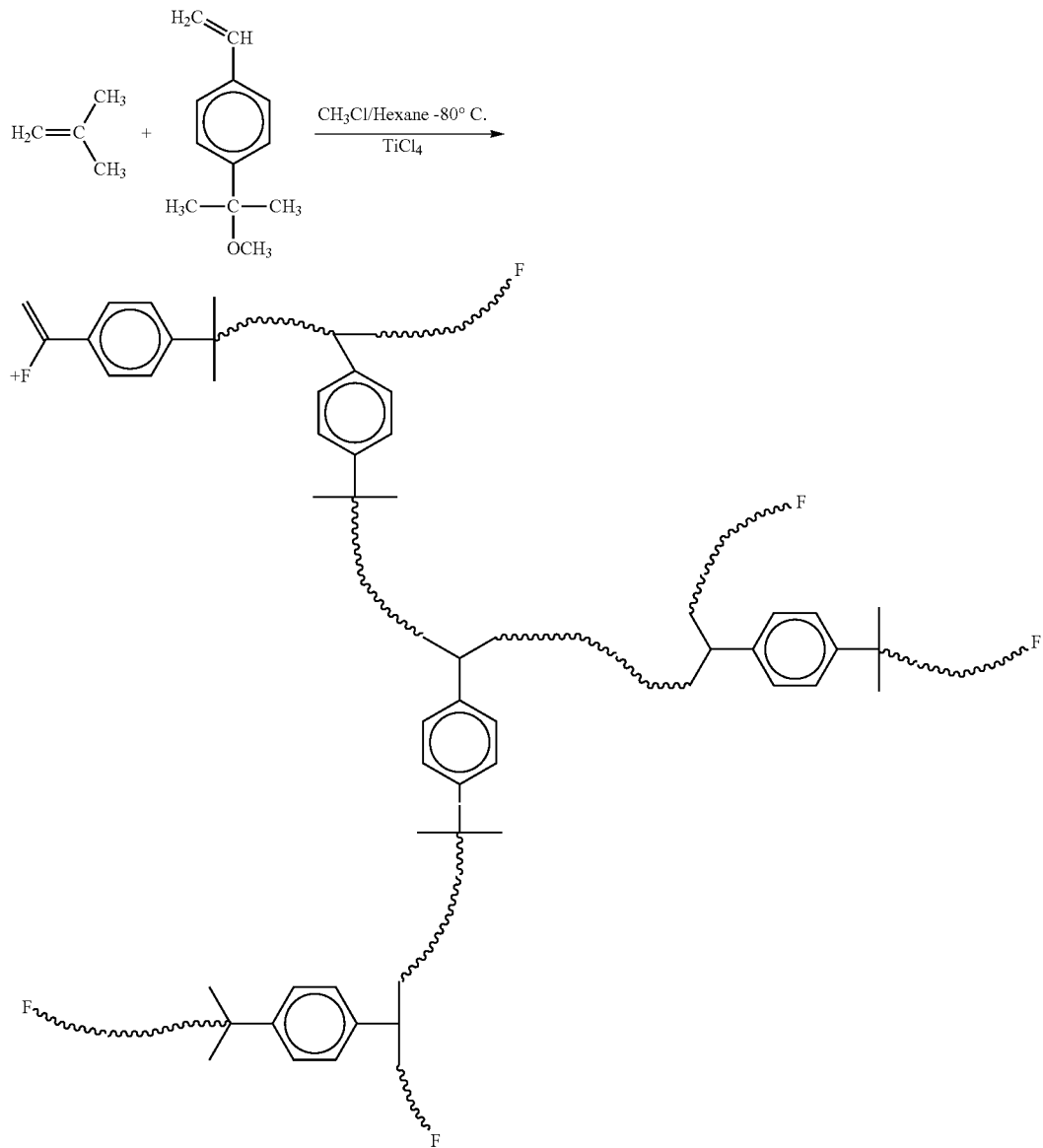

In still another embodiment, polymers for purification by the present invention can also include arborescent polymers formed from at least one inimer and at least one isoolefin that have been end-functionalized with about 0.5 to about 5 weight percent end blocks derived from a diene or diene derivative, or blocks of polydiene and polydiene derivatives.

In the polymers of U.S. Provisional Patent Application No. 60/841,757, such polymers can be formed from at least one inimer and at least one isoolefin. In one embodiment, the at

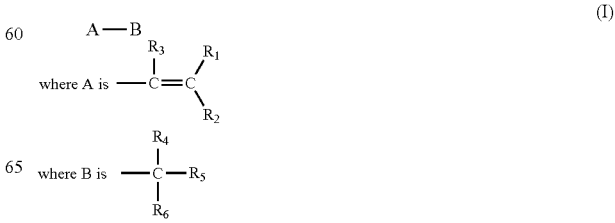

In Formula (I), $R_1$, $R_2$, $R_3$, $R_4$, $R_5$ and $R_6$ are each, in one embodiment, independently selected from hydrogen, linear or branched $C_1$ to $C_{10}$ alkyl, or $C_5$ to $C_8$ aryl. In another embodiment, $R_1$, $R_2$, and $R_3$ are all hydrogen. In another embodiment, $R_4$, $R_5$ and $R_6$ are each independently selected from hydrogen, hydroxyl, bromine, chlorine, fluorine, iodine, ester (—O—C(O)—$R_7$), peroxide (—OO$R_7$), and —O—$R_7$ (e.g., —OCH$_3$ or —OCH$_2$=CH$_3$). With regard to $R_7$, $R_7$ is an unsubstituted linear or branched $C_1$ to $C_{20}$ alkyl, an unsubstituted linear or branched $C_1$ to $C_{10}$ alkyl, a substituted linear or branched $C_1$ to $C_{20}$ alkyl, a substituted linear or branched $C_1$ to $C_{10}$ alkyl, an aryl group having from 2 to about 20 carbon atoms, an aryl group having from 9 to 15 carbon atoms, a substituted aryl group having from 2 to about 20 carbon atoms, a substituted aryl group having from 9 to 15 carbon atoms. In one embodiment, where one of $R_4$, $R_5$ and $R_6$ either a chlorine or fluorine, the remaining two of $R_4$, $R_5$ and $R_6$ are independently selected from an unsubstituted linear or branched $C_1$ to $C_{20}$ alkyl, an unsubstituted linear or branched $C_1$ to $C_{10}$ alkyl, a substituted linear or branched $C_1$ to $C_{20}$ alkyl, a substituted linear or branched $C_1$ to $C_{10}$ alkyl. In still another embodiment, any two of $R_4$, $R_5$ and $R_6$ can together form an epoxide.

In one embodiment, portions A and B of inimer compound (I) are joined to one another via a benzene ring. In one instance, portion A of inimer compound (I) is located at the 1 position of the benzene ring while portion B is located at either the 3 or 4 position of the benzene ring. In another embodiment, portions A and B of inimer compound (I) are joined to one another via the linkage shown below in Formula (II):

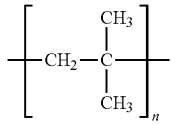

where n is an integer in the range of 1 to about 12, or from 1 to about 6, or even from 1 to about 3. In another embodiment, n is equal to 1 or 2.

In another embodiment, for isobutylene polymerization B can be a tertiary ether, tertiary chloride, tertiary methoxy group or tertiary ester. In one instance, very high molecular weight arborescent PIBs can be synthesized using the process of the present invention with inimers such as 4-(2-hydroxyisopropyl)styrene and 4-(2-methoxy-isopropyl)styrene.

Exemplary inimers for use in conjunction with at least one isoolefin to yield a polymer in accordance with U.S. Provisional Patent Application No. 60/841,757 include, but are not limited to, 4-(2-hydroxyisopropyl)styrene, 4-(2-methoxyisopropyl)styrene, 4-(1-methoxyisopropyl)styrene, 4-(2-chloroisopropyl)styrene, 4-(2-acetoxyisopropyl)styrene, 2,3,5,6-tertamethyl-4-(2-hydroxy isopropyl)styrene, 3-(2-methoxyisopropyl)styrene, 4-(epoxyisopropyl)styrene, 4,4,6-trimethyl-6-hydroxyl-1-heptene, 4,4,6-trimethyl-6-chloro-1-heptene, 4,4,6-trimethyl-6,7-epoxy-1-heptene, 4,4,6,6,8-pentamethyl-8-hydroxyl-1-nonene, 4,4,6,6,8-pentamethyl-8-chloro-1-nonene, 4,4,6,6,8-pentamethyl-8,9-epoxy-1-nonene, 3,3,5-trimethyl-5-hydroxyl-1-hexene, 3,3,5-trimethyl-5-chloro-1-hexene, 3,3,5-trimethyl-5-6-epoxy-1-hexene, 3,3,5,5,7-pentamethyl-7-hydroxyl-1-octene, 3,3,5,5,7-pentamethyl-7-chloro-1-octene, or 3,3,5,5,7-pentamethyl-7,8-epoxy-1-octene. In one embodiment, the inimer of the present invention is selected from 4-(2-methoxyisopropyl)styrene or 4-(epoxyisopropyl)styrene.

In still another embodiment, the at least one inimer utilized in conjunction at least one isoolefin to yield a polymer in accordance with U.S. Provisional Patent Application No. 60/841,757 has a formula according to one of those shown below:

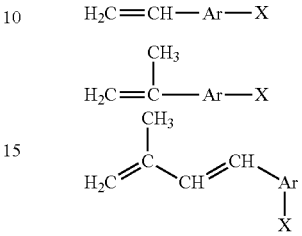

wherein X corresponds to a functional organic group from the series —C$R^1_2$Y, where Y represents O$R^1$, Cl, Br, I, CN, N$_3$ or SCN and $R^1$ represents H and/or a $C_1$ to $C_{20}$ alkyl, and Ar represents $C_6H_4$ or $C_{10}H_8$.

Formula (III) below details the nature of suitable isoolefin compounds that can be used in conjunction with at least one inimer to form a polymer in accordance with the disclosure contained in U.S. Provisional Patent Application No. 60/841, 757.

(III)

where $R_9$ is $C_1$ to $C_4$ alkyl group such as methyl, ethyl or propyl. In one embodiment, the compound according to Formula (III) is isobutylene (i.e., isobutene) or 2-methyl-1-butene.

In one embodiment, 4-(2-methoxyisopropyl)styrene or 4-(epoxyisopropyl) styrene is used as the inimer and isobutylene as the isoolefin, as is described in detail in U.S. Provisional Patent Application No. 60/841,757, which is incorporated herein by reference in its entirety.

In the polymers of U.S. Provisional Patent Application No. 60/841,757, the end-functionalized portion of these polymers can be derived from any suitable low or high glass transition polymer. Suitable polymers for accomplishing the end-functionalization of the present invention include, but are not limited to, homo or copolymer of styrene or styrene derivatives, including indene and its derivatives, diene or triene (conjugated or other dienes such as isoprene, butadiene-1,3; 2-methylbutadiene-1,3; 2,4-dimethylbutadiene-1,3; piperyline; 3-methylpentadiene-1,3; hexadiene-2,4; 2-neopentylbutadiene-1,3; 2-methlyhexadiene-1,5; 2,5-dimegyhexadiene-2,4; 2-methylpentadiene-1,4; 2-methylheptadiene-1,6; cyclopentadiene; methylcyclopentadiene; cyclohexadiene; 1-vinyl-cyclohexadiene; or mixtures of two or more thereof), norbornadiene, and β-pinene.

Accordingly, in one embodiment, the present invention relates to a method for purifying a block polymer that comprises: (a) dissolving the block polymer in a first solvent system to provide a first solution, wherein the first solvent system comprises one or more solvents, and the solvent system is capable of dissolving a polyisobutylene-based block polymer; and (b) combining the first solution with a second solvent system, wherein the second solvent system comprises one or more solvents, and the solvent system dissolves a polystyrene-based end block of the block polymer to a greater extent than it dissolves a polyisobutylene-based block of the block polymer, to provide a precipitated block polymer in a mother liquor.

In some embodiments of the present invention, combining the first solution with a second solvent system involves dropwise addition of the first solution into a large excess of the second solvent system. In one embodiment, the solvent of the first solution is tetrahydrofuran. In another embodiment, the method of the present invention can also include separating the precipitated block polymer from the mother liquor to provide a purified block polymer. In such cases where the method of the present invention involves the step of separating the precipitated block polymer from the mother liquor to provide a purified block polymer, such a step can, in one embodiment, include filtration or simple filtration.

In another embodiment, the method of the present invention can further include adding additional amounts of the second solvent system to the purified block polymer. This can be done prior to, or after, the mother liquor is decanted or otherwise separated from the precipitated polymer. In one such embodiment, the second solvent system is acetone. In another embodiment, the second solvent can be methyl ethyl ketone, methyl vinyl ketone, or the like. The addition of acetone, or another ketone, yields a mixture of the purified block polymer and acetone. In still another embodiment, the method of the present invention can further include adding a third solvent system to the mixture of the purified block polymer and acetone, wherein the third solvent system is a non-solvent with respect to at least two types of blocks of the purified block polymer, to provide a mixture of the purified block polymer and the mixture of solvents; and separating the purified block polymer from the mixture of solvents to provide a further purified block polymer.

In still another embodiment, the method of the present invention relates to a block polymer that comprises: (i) dissolving the block polymer in a first solvent system to provide a first solution, wherein the first solvent system comprises one or more solvents, and the solvent system is capable of dissolving a polyisobutylene-based polymer; (ii) combining the first solution with a second solvent system, wherein the second solvent system comprises one or more solvents, and the solvent system dissolves a polystyrene-based end block of the block polymer to a greater extent than it dissolves a polyisobutylene-based block of the block polymer, to provide a precipitated block polymer in a mother liquor; (iii) separating the precipitated block polymer from the mother liquor to provide a purified block polymer; (iv) adding acetone to the purified block polymer to provide a mixture of the purified block polymer and acetone; (v) adding a third solvent system to the mixture of the purified block polymer and acetone, wherein the third solvent system is a non-solvent with respect to at least two types of blocks of the purified block polymer, to provide a mixture of the purified block polymer and the mixture of solvents; and (vi) separating the purified block polymer from the mixture of solvents to provide a further purified block polymer.

In one embodiment, the above-mentioned third solvent system can include 2-propanol. Alternatively, the above-mentioned third solvent system can be 2-propanol exclusively, which is an excellent non-solvent to "shock" thermoplastic elastomers from solution.

In yet another embodiment, the method of the present invention relates to a block polymer that comprises: (A) dissolving about 1 part by weight of the block polymer in about 10 to 30 parts by weight of a first solvent system to provide a first solution, wherein the first solvent system comprises one or more solvents, and the solvent system is capable of dissolving a polyisobutylene-based polymer; (B) combining the first solution with about 5 to about 10 volumes of a second solvent system, with respect to the volume of the first solution, wherein the second solvent system comprises one or more solvents, and the solvent system dissolves a polystyrene-based end block of the block polymer to a greater extent than it dissolves the internal polyisobutylene-based blocks of the block polymer, to provide a precipitated block polymer in a mother liquor; (C) separating the precipitated block polymer from the mother liquor to provide a purified block polymer; (D) adding about 5 to about 10 volumes of acetone, with respect to the volume of the first solution, to the purified block polymer to provide a mixture of the purified block polymer and acetone; (E) adding about 1 to about 5 volumes, with respect to the volume of the first solution, of 2-propanol to the mixture of the purified block polymer and acetone, to provide a mixture of the purified block polymer and the mixture of solvents; optionally followed by adding an additional 1 to about 15 volumes of 2-propanol; and (F) separating the purified block polymer from the mixture of solvents to provide a further purified block polymer.

In some embodiments of the present invention, the second solvent system does not dissolve the polyisobutylene-based block of the block polymer to any appreciable extent, or at all, for example, such that the polyisobutylene-based block precipitates from the mother liquor under normal laboratory conditions, e.g., at about room temperature, etc.

The methods of the present invention can include drying the purified block polymer obtained from the various purification processes described herein (from the final step of any method, or at any point where the block polymer precipitates from a solvent). The drying can include subjecting the purified polymer to a reduced atmospheric pressure, to temperature above about 25° C., or both. In another embodiment, the temperature can be above about 30° C. but less than about 70° C., or even less than about 60° C.

In one embodiment, the polymers purified by the present invention can be a block polymer that is a thermoplastic elastomer (e.g., a polyisobutylene-based thermoplastic elastomer). In one embodiment, the polymers purified by the present invention can be a polyisobutylene-based thermoplastic elastomer, or even a polyisobutylene-based thermoplastic elastomer that is suitable for biomedical applications.

In another embodiment, the block polymers purified by the present invention can include polystyrene-based end-blocks. In one embodiment, the polystyrene-based end-block of such block polymers can be, for example, polystyrene, poly(styrene) wherein the benzene ring moiety of the styrene subunits are individually optionally substituted with one to five substituents, or a combination thereof. The optionally substituted benzene ring moieties of the styrene subunits can be one or more polystyrene blocks, poly(4-methylstyrene) blocks, poly (4-methoxystyrene) blocks, poly(4-tert-butylstyrene) blocks, poly(4-(2-hydroxyisopropyl)styrene) blocks, poly(4-(2-methoxyisopropyl)styrene) blocks, poly(3-(2-methoxyisopropyl)styrene) blocks, poly(4-(2-chloroisopropyl)styrene) blocks, poly(4-(2-acetylisopropyl)styrene) blocks, poly(4-(2-acetoxyisopropyl)styrene) blocks, poly(4-chlorostyrene) blocks, poly(4-(epoxyisopropyl)styrene) blocks, or a combination thereof.

In one embodiment, the first solvent system of the methods of the present invention can include one or more of tetrahydrofuran, methylcyclohexane, toluene, or benzene. In one instance, about 15 to about 25 volumes of the first solvent system can be used to initially dissolve the polymer to be purified in accordance with the methods of the present invention. In one instance, the polymer can be a block copolymer that includes one or more blocks derived from optionally substituted styrene monomers, and one or more blocks derived from isobutylene monomers. In one embodiment, the second solvent system of the methods of the present invention can be a ($C_3$ to $C_{10}$) ketone, a derivative thereof, or a combination of two or more thereof. In another embodiment, the second solvent system of the present invention can include acetone, methyl ethyl ketone, methyl vinyl ketone, or a combination thereof.

In one embodiment, the first solution and the second solvent system can be combined by dropwise addition of the first solution into the second solvent system. In one embodiment, the third solvent system can include an alcohol. In certain embodiments, the third solvent system does not dissolve either the polyisobutylene mid-block or the end blocks of the block polymer. The alcohol can include, but is not limited to, methanol, ethanol, 1-propanol, 2-propanol, or a $C_4$ alcohol (for example, tert-butanol or 1-butanol).

In one embodiment, the purified polymer obtained by the processes described herein, when isolated and dried, can contain less than about 20 parts per million, less than about 10 parts per million, less than about 5 parts per million, less than about 2 parts per million, less than about 1 part per million, or even less than about 0.5 part per million of any residual monomer. The purified polymer, for example, can contain less than about 5 parts per million of styrene monomers, para-methylstyrene monomers, para-methoxystyrene monomers, or any combination thereof, or the like.

In one embodiment, an antioxidant can be employed in the first solution. The antioxidant can be a vitamin or an antioxidant suitable for use in biomedical implants. The vitamin can specifically be vitamin A, vitamin C, or vitamin E.

In one embodiment, the separating in step (iii) or (C), or any separating step mentioned above, can include decanting, draining, or filtering. In one embodiment, the block polymer can be an arborescent copolymer comprising one or more styrene polymeric blocks in combination with one or more isobutylene polymeric blocks. In another embodiment, the block polymer can be a highly branched block copolymer that includes a polyisoolefin block and a polymonovinylidene arene block. In still another embodiment, the block polymer can have thermoplastic elastomeric properties. In another embodiment, the methods described herein can further include applying the purified polymer to a medical devise, or using the polymer in an implant.

Thus, in one embodiment, the present invention relates to branched or arborescent polymer compounds that contain one or more styrene polymeric blocks in combination with one or more isobutylene polymeric blocks. In another embodiment, the present invention relates to methods for purifying branched block or arborescent polymer compounds that contain at least one styrene polymeric block in combination with at least one isobutylene polymeric block.

In various embodiments of the invention, the methods of purification described herein reduce the drying time of the block polymer. In several embodiments, the drying time for certain block copolymers is reduced from about 1 to about 2 months, down to only 24 hours, and often less than 24 hours. The reduced drying rate can be attributed to the fact that polymers are difficult to dry when polyisobutylene blocks orient on the outside of a polymer matrix when the block polymer is separated from a mother liquor (e.g., by precipitation, filtration, etc.).

Given the above, in one embodiment the phase inversion techniques described herein thus provide purified polymers wherein polyisobutylene blocks orient themselves at the inside of the polymer matrix when the block polymer is separated from a mother liquor. This can be a result of the Step (b), (ii) or (B) described above wherein the second solvent system is combined with the dissolved polymer, resulting in the precipitation of the block polymer and concomitant purification (e.g., removal of residual monomers such as styrene or styrene derivatives), as well as affording the faster drying properties to the purified block polymer.

As is discussed above, the polymers purified by the present invention can be thermoplastic elastomers that contain both styrene and isobutylene polymeric blocks/units. Thermoplastic elastomers containing one or more elastomeric polyisobutylene blocks are extremely useful materials due in part to the saturated nature of their midblock segments. They exhibit a unique combination of properties including a high degree of resistance to penetration by either moisture or gases, together with a high degree of thermal and oxidative stability. The products also exhibit a self-reinforcing characteristic as a result of the fact that the glassy blocks and the elastomeric blocks show phase separation.

Exemplary Polymer Preparation:

The following is an example of a polymer preparation method for preparing a suitable polymer for purification via a method in accordance with the present invention. However, the present invention is not limited to just the following polymer, or polymers. Rather, any of the above-mentioned polymers can be purified via a method in accordance with the present invention. Additionally, any suitable preparation method can be utilized to produce such polymer compounds for purification via the methods of the present invention.

In preparing thermoplastic elastomers the polymerization reaction is conducted under conditions that typically avoid chain transfer and termination of growing polymer chains. In one embodiment, anhydrous conditions are utilized and reactive impurities, such as components containing active hydrogen atoms (water, alcohol and the like) are removed from both the monomer and solvents using techniques known by those of ordinary skill in the art. The temperature at which the polymerization reaction is conducted is, in one embodiment, between about $-10°$ C. and about $-100°$ C., or from about $-30°$ C. and about $-90°$ C., or even from about $-40°$ C. and about $-80°$ C., although lower temperatures may be employed if desired. In order to avoid moisture condensation the reaction can, if so desired, be carried out under a dry inert gas atmosphere, such as nitrogen gas or argon.

In one embodiment, the invention provides a branched block copolymer of a polyisoolefin containing more than one branch point per chain and a polymonovinylidene arene that is characterized by having thermoplastic elastomeric properties. The branched block copolymer can include a branched polyisoolefin block. Some of the branches of the aforesaid polyisoolefin block can terminate in polymonovinylidene arene end-blocks. In addition to the term "highly branched", the terms "arborescent" and "hyperbranched" also may be used to describe the structure of various polymers disclosed herein. For example, the highly branched or arborescent polymers can have an irregular tree-like structure.

In one embodiment, the highly branched block copolymers that have been found to exhibit thermoplastic elastomeric properties contain a highly branched polyisoolefin midblock that is synthesized using a process that involves use of an amount of inimer, a compound carrying both an initiator and a monomer functionality ("IM"), which is copolymerized with an olefin. An inimer can be used to initiate polymerization and to introduce random branching points in elastomeric mid-blocks. The inimer can be represented by the general formula A-B, where A is a polymerizable function, such as a vinylic double bond, and B is an initiating group.

For isobutylene polymerization B can be, in one embodiment, a tertiary ether, tertiary chloride, tertiary methoxy group, tertiary ester, an epoxide, or any other suitable initiator for isobutylene polymerization. Very high molecular weight arborescent polyisobutylenes can be synthesized using this method.

In one embodiment, compounds that can be used as the IM include, but are not limited to, 4-(2-hydroxyisopropyl)styrene and 4-(2-methoxyisopropyl)styrene. An example reaction is shown below in Scheme 1 where the IM utilized is 4-(2-methoxyisopropyl)styrene.

Scheme 1

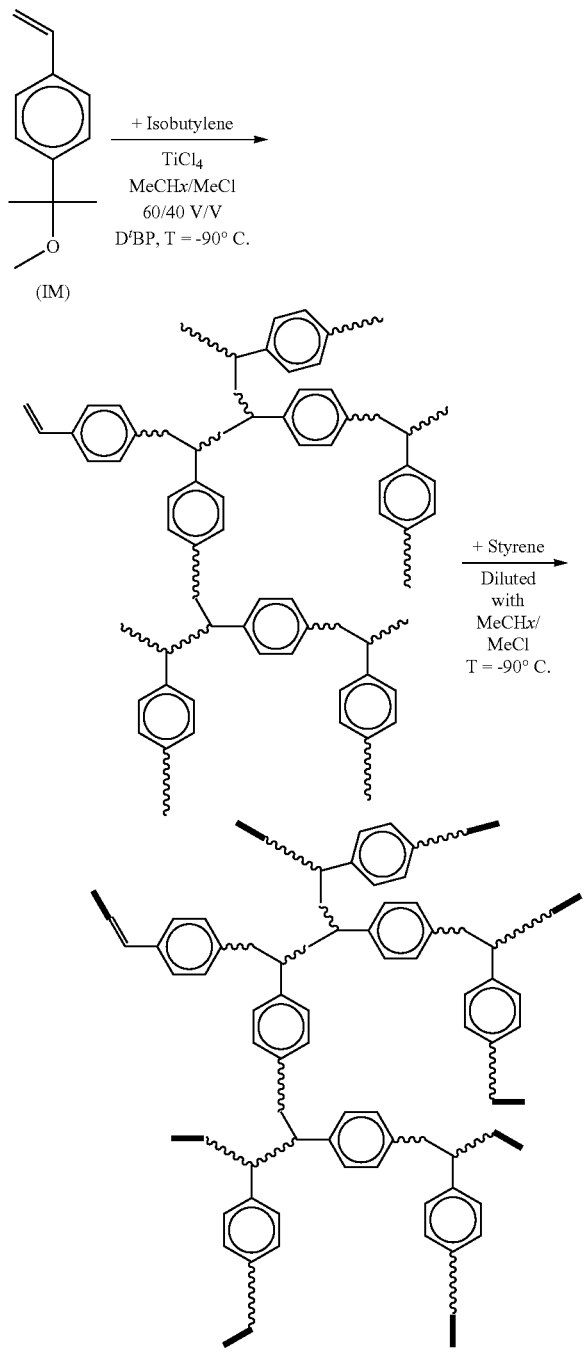

Of course, other inimers can be used in reactions similar to Scheme 1. In certain embodiments 4-(2-hydroxyisopropyl) styrene; 4-(2-methoxy isopropyl) styrene; 4-(2-chloroisopropyl)styrene; 4-(2-acetoxyisopropyl)styrene; 2,3,5,6-tertamethyl-4-(2-hydroxy isopropyl)styrene; 3-(2-methoxyisopropyl)styrene; 4-(epoxy isopropyl)styrene; 4,4,6-trimethyl-6-hydroxyl-1-heptene; 4,4,6-trimethyl-6-chloro-1-heptene; 4,4,6-trimethyl-6,7-epoxy-1-heptene; 4,4,6,6,8-pentamethyl-8-hydroxyl-1-nonene, 4,4,6,6,8-pentamethyl-8-chloro-1-nonene; 4,4,6,6,8-pentamethyl-8,9-epoxy-1-nonene; 3,3,5-trimethyl-5-hydroxyl-1-hexene; 3,3,5-trimethyl-5-chloro-1-hexene; 3,3,5-trimethyl-5-6-epoxy-1-hexene; 3,3,5,5,7-pentamethyl-7-hydroxyl-1-octene, 3,3,5,5,7-pentamethyl-7-chloro-1-octene; 3,3,5,5,7-pentamethyl-7,8-epoxy-1-octene, or combinations thereof, can be used as the IM in variations of Scheme 1 shown above.

In this embodiment, the isoolefins that are used in the synthesis of the highly branched polyisoolefin include those with the formula $CH_2=C(CH_3)-R$ where R represents a $C_1$ to $C_{20}$ linear or branched alkyl group, or a $C_1$ to $C_{10}$ linear or branched alkyl group, or even a $C_1$ to $C_4$ linear or branched alkyl group such as methyl, ethyl or propyl. In another embodiment, the polyisoolefin is isobutylene or 2-methyl-1-butene. In still another embodiment, polyisobutylene is utilized.

The monovinylidene arenes suitable for the production of the polyvinylidene blocks that form the endblocks on some of the branches of the highly branched polyisoolefin include, but are not limited to, $C_8$ to $C_{12}$ monovinylidene arenes that can be substituted with one to five $C_1$ to $C_{12}$ alkyl or alkoxy group or one to five fluorine, chlorine, bromine or iodine atoms, or a combination thereof, on the aromatic ring. In one embodiment, the mono-vinylidene arenes can be styrene, p-methylstyrene, p-tert-butylstyrene, p-chlorostyrene, indene, or the various mixtures thereof. In still another embodiment, styrene is used.

The highly branched polyisoolefin that is used as a basis for producing the highly branched block copolymers have a branching frequency of from about 2 to about 60, or even from about 8 to about 35. In one embodiment, the branching frequency is more than one. In order that the highly branched block copolymers exhibit thermoplastic elastomeric properties it is desirable, in one embodiment, that the weight percent of the polymono-vinylidene arene endblocks in the block copolymers is in the range of from about 0.5 to about 50 weight percent.

The number average molecular weight, $M_n$, of the highly branched polyisoolefins can be from about 10,000 to about 2,000,000, or even from about 500,000 to about 1,000,000. The molecular weight distribution of the highly branched polyisoolefin can be from about 1 to about 20, or even from about 1.2 to about 2.8.

The process according to the invention can be, in one embodiment, carried out in an inert organic solvent or solvent system (solvent mixture or solution of two or more solvents) in order that the highly branched polyisoolefin and the final block copolymer remain in solution and at the same time there is some degree of polarity so that the polymerization proceeds at a reasonable rate. In order to fulfill these requirements a single solvent such as n-butyl chloride can be used, or a mixture of a non-polar solvent and a polar solvent can be used. Suitable non-polar solvents include, but are not limited to, methylcyclohexane and cyclohexane and appropriate polar solvents include ethyl chloride, methyl chloride and methylene chloride. In one embodiment, the solvent can be a mixture of methylcyclohexane and methyl chloride. To achieve suitable solubility and polarity it has been found that the ratio of the non-polar solvent to the polar solvent on a weight basis should be from about 80:20 to about 40:60, or even about 60:40.

As is noted above, the temperature range at which a reaction can be carried out is from about −10° C. and about −100° C., or from about −30° C. and about −90° C., or even from about −40° C. and about −80° C., although lower temperatures may be employed if desired. One procedure is preferably carried out using a 1 to about 30 percent polyisoolefin solution (weight/weight basis), or even from about 5 to about 10 weight percent.

In order to produce highly branched block copolymers it is often necessary to employ a co-initiator, such as a Lewis acid halide. Suitable Lewis acid halides include, but are not limited to, boron trichloride, aluminum trichloride, and titanium tetrachloride. The ratio of the co-initiator to the monovinylidene arene on a molar basis can be from about 1:1 to about 1:30, or even from about 1:10 to about 1:20, or any of the various ranges in between.

The branched block copolymers may also be produced in a one-step process wherein the isoolefin is copolymerized with the initiator monomer in conjunction with the co-initiator in a solution at a temperature of from about −20° C. to about −100° C. An electron donor and a proton trap are subsequently introduced, followed by the addition of a pre-chilled solution of the monovinylidene arene in the solvent and the polymerization is allowed to continue until it is terminated by the addition of a pre-chilled nucleophile such as methanol. The polymerization reaction is allowed to proceed for a preselected period of time prior to being terminated in order to produce the arborescent branched block copolymer in accordance with various embodiments.

Alternatively, in order to connect two or more of the arborescent structures, the polymerization process can be allowed to continue after all the styrene is consumed, as disclosed in U.S. Pat. No. 5,721,331, which is incorporated herein by reference in its entirety. This patent discloses that when the polymerization process is continued after the styrene monomer is consumed, the active living chain ends can attack the styrene block of another chain, creating multiblocks with each block being one of the arborescent blocks. The individual arborescent branched block copolymers are bound together wherein at least one of the polymonovinylidene arene plastic endblocks on one arborescent branched block copolymer is chemically bound to one polymonovinylidene arene plastic endblock on another arborescent branched block copolymer. Thus when multiblocks are the desired end product, the polymerization reaction is allowed to proceed for a longer period of time prior to terminating the polymerization reaction by addition of a suitable nucleophile.

The production of the highly branched block copolymers necessitates the use of additives such as electron pair donors to improve blocking efficiency and proton traps to minimize homopolymerization. Examples of suitable electron pair donors are those nucleophiles that have an electron donor number of at least 15 and no more than 50 as tabulated by Viktor Gutmann in "The Donor Acceptor Approach to Molecular Interactions", Plenum Press (1978) and include, but are not limited to, ethyl acetate, dimethylacetamide, dimethylformamide and dimethyl sulfoxide. Suitable proton traps include, but are not limited to, 2,6-ditertiarybutylpyridine, 4-methyl-2,6-di-tert-butylpyridine and diisopropylethylamine.

The degree of branching of the polyisoolefin, the molecular weight distribution of the polyisoolefin, the weight ratio of the coinitiator to the polyisoolefin, the molar ratio of the co-initiator to the monovinylidene arene, the reaction temperature and the reaction time may affect the extent to which endblocking of the polyisoolefin branches occurs. As a consequence by varying some of the aforementioned parameters it is possible to produce branched block copolymers with different thermoplastic elastomeric properties.

Purification:

The invention provides a purification method for a copolymer product. In one instance the copolymer product that is purified is a polyisobutylene-polystyrene copolymer. However, the purification method is not limited solely to branched copolymer products that include at least one polyisobutylene polymer functionality and at least one polystyrene functionality. Rather, in one embodiment, the purification method can be used in conjunction with any copolymer of polyisobutylene, and polystyrene or a polystyrene derivative. These polymers can be the linear, branched, star-shaped, and the like. Many such types of blocks and block polymers that can be purified by the methods described herein can be found in the patent documents listed in herein.

In another embodiment, the purification method of the present invention can be used in conjunction with any polymer, copolymer, or block copolymer as is discussed above.

Those of skill in the art in the field of block polymer preparation are well aware that polyisobutylene-based polymers are very hard to purify and dry. One reason for this is that polyisobutylene-based blocks are extremely impermeable forms of rubber. Traditionally, polymers high in polyisobutylene-based block content are precipitated in alcohol or water. The resulting solid forms a rubber crumb that often takes two or three weeks, often one or two months, to fully dry. In these situations, the polyisobutylene is the continuous phase in the block. In contrast, by employing the process described herein, a plastic-like flake is obtained upon precipitation/decanting/filtration, because the disclosed procedure allows for a block orientation such that the end blocks become the continuous phase.

Among other benefits, the purification method can reduce the concentration of unreacted monomers, initiators and co-initiator residues that remain in the polymer matrix once the polymerization reaction is complete. Additionally, the purification process significantly decreases the time required to completely dry the isolated polymer after isolation, or to sufficiently dry the polymer such that it can be employed in biomedical applications. Thus, the purification process enables the production of copolymer products that are purified to such an extent as to be useful in biomedical and/or pharmaceutical applications. Additionally, the purification process decreases the length of time required to process and dry to polymer in preparation for use in biomedical and/or pharmaceutical applications.

An example reaction scheme and method by which to purify the reaction products are provided in the Examples below. The purification method is able to generate products suitable for biomedical and/or pharmaceutical applications.

EXAMPLES

Example 1

Polymer Preparation

The preparative reaction targeted making approximately 400 grams of poly(isobutylene)-poly(styrene) ("PIB-PS") copolymer with 30 wt % PS, $M_n$=215,000 g/mol and BR=10 (average number of branching points per PIB chain). The reaction illustrated below in Scheme 1 will be used as an example of the various preparative processes.

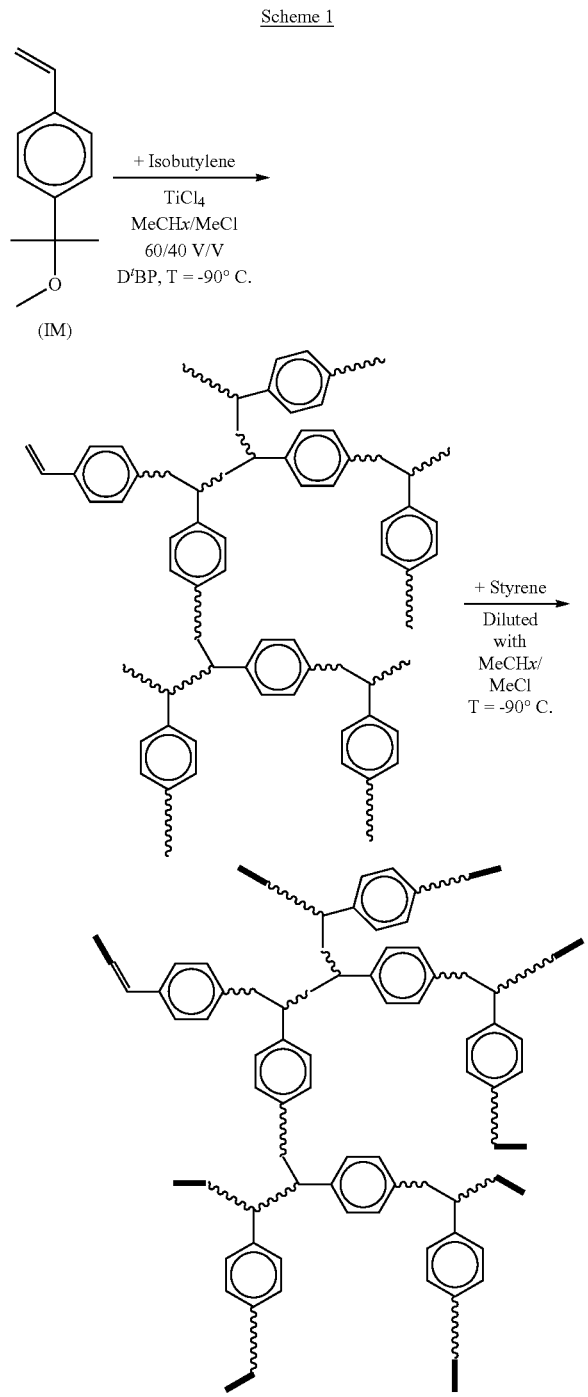

Scheme 1

Materials:

Isobutylene (IB): 99.9%; methyl chloride (MeCl): 99.9%; initiator (IM): 4-(2-methoxy-isopropyl)styrene ("MeOIM") or 4-(1,2-oxirane-isopropyl)styrene ("EPOIM"), synthesized at the University of Akron; methylcyclohexane ($MeCH_x$); 2,6-di-tertiary-butyl pyridine (DtBP)—dry; dimethyl acetamide (DMA); titanium tetrachloride ($TiCl_4$); and styrene: polymerization grade.

First Step (IB Homopolymerization):

| Chemicals | Molecular Weight (g/mol) | Density (g/mL) | Conc. (mol/L) | Mass (g) | Volume (mL) |
|---|---|---|---|---|---|
| $MeCH_x$ | 98.19 | 0.77 | | | 1800 |
| MeCl | 50.49 | 1.119 | | | 1200 |
| DtBP | 191.32 | 0.852 | | | 4 |
| IM | 176.25 | 1.4 | 0.0025 | 1.4 | 1 |
| $IB_o$ | 56.11 | 0.705 | | 84.6 | 120 |
| $TiCl_4$ | 189.68 | 1.73 | 0.049 | | 17 |
| Additional solvent | $MeCH_x$ with $TiCl_4$ | | | | 50 |
| Total | | | | Σ | 3192 |
| $2^{nd}$ portion of IB | | | | 84.6 | 120 |
| $3^{rd}$ portion of IB | | | | 84.6 | 120 |
| DtBP | | | | | 1 |
| DMA 87.12~1 | | | | | 1.7 |
| Total | | | | | 3192 |

Second Step (Styrene Addition):

| Chemicals | Molecular Weight (g/mol) | Density (g/mL) | Conc. (mol/L) | Mass (g) | Volume (mL) |
|---|---|---|---|---|---|
| Styrene | 104.15 | 0.909 | | | 350 |
| MeCl | | | | | 150 |
| MeCHx | | | | | 250 |
| DtBP | | | | | 1 |
| Total | | | | Σ | 3942 |

Polymerization temperature: −90° C. with reaction monitoring via a thermocouple.
Procedure:
1) Add 1.4 grams of inimer (either MeOIM or EPOIM) into a 5 L three neck flask;
2) Add 1800 mL of $MeCH_x$;
3) Add 1200 mL condensed MeCl;
4) Add 4 mL di-tert-butyl pyridine;
5) Add 120 mL IB;
6) Start polymerization by the addition of 17 mL $TiCl_4$ dissolved in 50 mL $MeCH_x$, cooled to reaction temperature before addition);
7) Monitor temperature and wait until temperature levels off and is steady at −90° C. (approximately 25 minutes);
8) Add 120 mL IB;
9) Wait until temperature levels off and is steady at −90° C. (approximately 25 minutes);
10) Add 120 mL IB;
11) Wait until temperature levels off and is steady at −90° C. (approximately 25 minutes);
12) Add 120 mL IB;
13) Add 1.0 mL di-tert-butyl pyridine;
14) Add 1.7 mL anhydrous dimethyl acetamide;
15) At forty minutes after the addition of the last IB portion add a pre-chilled mixture of 250 mL $MeCH_x$, 350 mL St, 150 mL of MeCl and 1 mL di-tert-butyl pyridine. Add St to $MeCH_x$ first, cool solution and add MeCl. Agitate to avoid freezing of the mixture;
16) Continue polymerization for 45 more minutes;
17) Add isopropanol NaOH solution to terminate reaction. (250 mL i-PrOH+22 grams NaOH for 15 mL $TiCl_4$);

18) Before MeCl boils up, transfer the reactor content into 12 L flask;

19) Use THF to remove scar from reactor and combine organic phases.

Then, wash solution with water until neutral; and

20) Remove TiCl$_4$ by filtration/centrifugation.

Recovery:

21) Add spatula-tip-full of Irganox 1076 antioxidant into a 4000 mL beaker;

22) Place 2000 mL acetone into the beaker;

23) Add 300 mL polymer solution (about 5 wt % in THF) with agitation;

24) Agitate for 2 minutes;

25) Let solution sit for 5 minutes, then decant liquor to waste vessel;

26) Add 2000 mL acetone with stirring; stir for 2 minutes;

27) Add 500 mL isopropanol—let is sit for 5 minutes to settle;

28) Quickly fill the beaker with isopropanol ("shock" the mixture);

29) Decant liquor to waste;

30) Leave to settle—fluffy white solid, clear solution;

31) Filter to remove liquid (suction); and

32) Spread fluffy solid on drying trays, dry it under vacuum for 1 to 2 days.

Example 2

Polymer Purification

Polymers targeted for biomedical applications need to be purified carefully to remove residual monomers and solvents. In this example a procedure is disclosed using phase inversion that reduces the residual styrenic monomer content in PIB-based styrenic block copolymers to less than 5 ppm, and allows for quick drying of these materials.

Materials:

Methyl chloride (MeCl) and isobutylene (IB) (provided by Lanxess) are dried by passing the gases through a column filled with BaO and CaCl$_2$ before condensing them at the polymerization temperature. Methyl cyclohexane (MeCH$_x$) and hexane (Hx) are distilled from CaH$_2$ prior to use. Titanium tetrachloride (TiCl$_4$), 2,6-di-tert-butyl pyridine (DtBP) and N,N-dimethyl acetamide (DMA) (Aldrich) are used as received. p-Methyl styrene (p-MeSt) (Aldrich) is purified by chromatography. 4-(2-Methoxyisopropyl)styrene (MeOIM) and 4-(1,2-epoxyisopropyl)styrene (EPOIM) were synthesized as is known in the art.

Polymerizations:

The polymerization reactions are carried out at −95° C. in a round-bottom flask equipped with an overhead stirrer in a dry box (Mbraun LabMaster 130) under a dry nitrogen atmosphere. The moisture (<1 ppm) and oxygen (<5 ppm) content is continuously monitored.

Purification Process:

The final product is purified by precipitation of approximately 300 mL of the final solution in 3,000 mL of acetone and, after decanting the product, adding 2 to 3 liters of methanol and decanting and filtering the product. Specifically, a spatula-tipful of Irganox 1076 (an antioxidant) is placed into a 4000 mL beaker and 2000 mL acetone is added. A 300 mL amount of the polymer solution (about 5 wt. % in THF) is added dropwise with agitation. The slurry is agitated for 2 minutes, let to sit for 5 minutes, then the liquor is decanted into a waste vessel. Next, 2000 mL acetone is added to the solids with stirring for 2 minutes. Then 500 mL isopropanol is added and the slurry is allowed to sit for 5 minutes to settle. The beaker is then quickly filled with isopropanol ("shock" the mixture). The liquor is decanted to waste and the fluffy white solid is filtered, spread on drying trays and allowed to dry under vacuum for 1 to 2 days.

Measurement of Residual Styrenic Monomer Content:

Residual styrene ("St") and para-methylstyrene ("pMeSt") levels are determined using the following procedures: Block copolymer samples are placed in a known amount of hexane, with nonane as an internal standard. The samples are swollen (dendritic block) or dissolved (linear triblocks) after keeping them on a shaker overnight. The samples are then coagulated with methanol, and the supernatant is then analyzed using a HP6890 GC equipped with an auto-injector, a flame ionization detector (FID) and a Restek RTX-1 column (30 m×0.32 mm×1 μm). The flow rate is kept constant at 2.5 mL/min, with splitless injection of 75 mL at 2 minutes. The oven program started at 40° C. with 7 minutes of holding time, and is ramped up by 20 C/minute to a final temperature of 250° C. where it is held for 5 minutes.

Characterization:

The samples are analyzed by Size Exclusion Chromatography (SEC). The system consisted of a Waters 515 HPLC pump, a Waters 2487 Dual Absorbance Detector, a Wyatt OPTILAB DSP Interferometric Refractometer, a Wyatt DAWN EOS multi-angle light scattering detector, a Wyatt ViscoStar viscometer, a Wyatt QELS quasi-elastic light scattering instrument, a Waters 717-plus autosampler and 6 Styragel® columns (HR0.5, HR1, HR3, HR4, HR5 and H6).

The RI detector and the columns are thermostatted at 35° C. THF freshly distilled from CaH$_2$ is used as the mobile phase at a flow rate of 1 mL/minute. The results are analyzed using the ASTRA software (Wyatt Technology), using refractive index increment dn/dc=0.108 for the arbPIB. The dn/dc values for the block copolymers are calculated using copolymer compositions determined by $^1$H NMR. The dn/dc value for p-MeSt is not available in the literature; therefore polystyrene dn/dc=0.183 is used in calculations. Standard polystyrene with 30,000 g/mol (PS30) is used to check the SEC system.

$^1$H NMR is performed using a Bruker Avance 500 or a Varian Mercury 300 instrument in various solvents such as deuterated THF, C$_6$D$_6$ and CDCl$_3$. Copolymer composition is determined from the relative integrals of corresponding aromatic and aliphatic peaks.

arbPIB-b-PS (05DNX120):

The reaction is performed at −90° C. in a mixture of solvents Hx/MeCl 60/40 v/v. The total volume is 3,000 mL. The copolymerization commences with the introduction of TiCl$_4$ (6.1×10$^{-2}$ mol/L) into the reactor containing IB (85.5 grams, 4.8×10$^{-1}$ mol/L), MeOIM (1.2×10$^{-3}$ mol/L) and DtBP (5.6× 10$^{-3}$ mol/L) as a proton trap in the solvent mixture (Hx/MeCl 60/40 v/v). Twenty-five minutes after the polymerization is initiated, a sample is taken and another increment of IB is added. This step is repeated two more times. Finally, a sample is taken 35 minutes after the fourth IB increment.

The conversion obtained by gravimetry right before each IB addition is 100%. The final total concentration of IB in the reactor is 2 mol/L. After all IB reacts, a pre-chilled solution of 350 mL of styrene in 150 mL of MeCl and 250 mL of Hx, containing also 1.7 mL of DMA and 2 mL of DtBP is added. The polymerization is terminated 45 minutes after the styrene addition with a solution of NaOH in methanol. The reactor is removed from the dry box and placed into a fume hood to allow for the evaporation of the solvents. The polymer is purified using a process according to the present invention.

The final sample has a $M_n$=220,300 g/mol, $M_w$=412,000 g/mol, MWD=1.87, PS=29.4 wt %.

arbPIB-b-PS (05DNX130):

Sample 05DNX130 is synthesized similar to Sample 05DNX120 but the concentration of MeOIM is doubled. The reaction is performed at −90° C. in a mixture of solvents Hx/MeCl 60/40 v/v. The total volume is 3,000 mL. The copolymerization commences with the introduction of TiCl$_4$ (4.9×10$^{-2}$ mol/L) into the reactor containing IB (85.5 grams, 4.8×10$^{-1}$ mol/L), IM (2.51×10$^{-3}$ mol/L) and DtBP (5.6×10$^{-3}$ mol/L) as a proton trap in the solvent mixture (Hx/MeCl 60/40 v/v). Twenty-five minutes after the polymerization is initiated a sample is taken and another increment of IB is added. This step is repeated two more times. Finally, a sample is taken 35 minutes after the fourth IB increment.

The conversion obtained by gravimetry right before each IB addition is 100%.

The final total concentration of IB in the reactor is 2 mol/L. After all IB reacts, a pre-chilled solution of 350 mL of styrene in 150 mL of MeCl and 250 mL of Hx, containing also 1.7 mL of DMA and 2 mL of DtBP is added. The polymerization is terminated 45 minutes after the styrene addition with a solution of NaOH in methanol. The reactor is removed from the dry box and placed into a fume hood to allow for the evaporation of the solvents. The polymer is purified using a process according to the present invention. The final sample has a $M_n$=163,200 g/mol, $M_w$=395,500 g/mol, MWD=2.54, PS=34.3 wt %.

arbPIB-b-P(pMeSt) (06DNX040):

The copolymerization commences with the introduction of TiCl$_4$ (5.99×10$^{-2}$ mol/L) into the reactor containing IB (85.5 grams, 4.77×10$^{-1}$ mol/L), IM (1.24×10$^{-3}$ mol/L) and DtBP (5.57×10$^{-3}$ mol/L) as a proton trap in the solvent mixture (MeCHx/MeCl 60/40 v/v). Sequential addition of three more aliquots (85.5 grams each) of IB is performed to grow the IB chains after the branches have formed. Complete conversion of IB is reached before each sequential addition.

The overall IB concentration is 2 mol/L. After all IB reacts, 350 mL pre-chilled p-MeSt (50% in MeCH$_x$/MeCl (60/40 v/v), DtBP (2.09×10$^{-2}$ mol/L) and DMA (4.28×10$^{-2}$ mol/L) are introduced into the system. The reaction is terminated with a solution of NaOH in methanol. The reactor is removed from the dry box and placed into a fume hood to allow for the evaporation of the solvents. The polymer is purified using the new procedure. The final product has 31 wt % P(p-MeSt); $M_n$=302.600 g/mol, MWD=2.56.

arbPIB-b-P(pMeSt) (06DNX120):

The reaction is performed at −90° C. in a mixture of solvents Hx/MeCl 60/40 v/v. The total volume is 1500 mL. The copolymerization commences with the introduction of TiCl$_4$ (3.13×10$^{-2}$ mol/L) into the reactor containing IB (240 mL, 1.74 mol/L), IM (2.28×10$^{-2}$ mol/L) and DtBP (5.1×10$^{-2}$ mol/L) as a proton trap in the solvent mixture (Hx/MeCl 60/40 v/v).

After all IB reacts, a pre-chilled solution of 70 mL p-methylstyrene in 150 mL of MeCl and 250 mL of Hx, containing also 1.0 mL of DMA and 1 mL of DtBP is added. The polymerization is terminated 45 minutes after the styrene addition with a solution of NaOH in methanol. The reactor is removed from the dry box and placed into a fume hood to allow for the evaporation of the solvents. The polymer is purified using the new process. The final sample has a $M_n$=137,600 g/mol, MWD=1.52, and 16.5 wt % PpMeSt.

When the block copolymers are precipitated from acetone using a procedure as described herein, fluffy white polystyrene-like flakes are obtained that dried completely within a day. GC analysis shows less then five ppm residual St or pMeSt, and often residual styrenic monomers are not detected at all (Table 1). In contrast, polymers precipitated from methanol and dried on a press at 100° C. have about 400 ppm residual styrenic monomers. Heating the press to 180° C. reduces the residuals to about 200 ppm. Because the styrenic monomers have the highest boiling point of the ingredients used in the synthesis process, these results demonstrate the effectiveness of the new purification process.

Table 1 details the purification of commercial linear polystyrene-polyisobutylene-polystyrene triblock copolymers (SIBS from the Kaneka Co., Japan) and arbPIB-based block copolymers with polystyrene and poly(para-methylstyrene) end blocks.

TABLE 1

| Sample ID | End Block (EB) | EB Content (wt %) | Residual Monomer (ppm) | Comment |
|---|---|---|---|---|
| Kaneka 073T | PS | 30 | 3.10 | Commercial Triblock SIBS |
| Kaneka 103T | PS | 34 | 15.32 | Commercial Triblock SIBS |
| 05DNX120 | PS | 29.4 | 2.89 | Purified (using procedure described herein) |
| 05DNX120 | PS | 29.4 | 8.18 | Purified (using procedure described herein) + centrifuged |
| 05DNX130 | PS | 34.3 | 2.85 | Purified |
| 06DNX040 | PpMeSt | 31 | 408 | Coagulated + pressed at 100° C. |
| 06DNX040 | PpMeSt | 31 | 229 | Coagulated + pressed at 180° C. |
| 06DNX040 | PpMeSt | 31 | 224 | Stripped in vacuum |
| 06DNX040 | PpMeSt | 31 | 15 | Purified (using procedure described herein) |
| 06DNX040 | PpMeSt | 31 | 0 | Purified (using procedure described herein) |

Soxhlet Extraction of Sample 06DNX120 Purified by the Described Procedures:

(1) Methyl Ethyl Ketone MEK (to Remove PS):

The sample (approximately 10 grams) is cut into pieces and placed in the Soxhlet thimble. Next, 200 mL methyl ethyl ketone (Fluka≥99.5% (GC), K3520-16/4/201-puriss .p.a.) is placed into a round bottom flask. The extraction is carried out and the solvent is allowed to pass through the sample 10 times. The extracted sample is placed into a Petri dish and dried in a vacuum oven set at 50° C. until constant weight is obtained. Three samples are extracted.

(2) Hexane Hx (to Remove PIB):

The sample (approximately 10 grams) is cut into pieces and placed in the Soxhlet thimble. Next, 200 mL Hx—Polskie odczynniki chemiczne S.A (serial number 0178/07/04, catalog number—466400426) is placed into a round bottom flask. The solvent is allowed to pass through the sample 10 times. The extracted sample is placed into a Petri dish and allowed to dry in a vacuum oven set at 50° C. until constant weight is obtained. Three samples are extracted.

(3) Ethanol EtOH (to Remove Polar Compounds):

The sample (approximately 10 grams) is cut into pieces and placed in the Soxhlet thimble. Next, 200 mL EtOH (from POCH—Ethyl Alcohol, 96% pure, p.A. Catalog number—396420113) is placed into a round bottom flask. The solvent is allowed to pass through the sample 12 times. The extracted sample is placed into a Petri dish and allowed to dry in a vacuum oven set at 50° C. until constant weight is obtained. Three samples are extracted.

After the above extractions, no extractables are found within experimental error (<0.3% wt % loss). The molecular weight and molecular weight distribution of the sample before and after extraction also remains unchanged—$M_w$=203,100 g/mol (before 204,300 g/mol), MWD=1.45 (before 1.41).

Although the invention has been described with reference to certain embodiments detailed herein, other embodiments can achieve the same or similar results. Variations and modifications of the invention will be obvious to those skilled in the art and the invention is intended to cover all such modifications and equivalents.

What is claimed is:

1. A method for purifying a block copolymer comprising the steps of:
   (a) providing an arborescent block copolymer comprising a polyisobutylene-based thermoplastic elastomer having polystyrene based end blocks;
   (b) dissolving the block copolymer in a first solvent system to provide a first solution, wherein the first solvent system comprises one or more solvents capable of dissolving a polyisobutylene-based polymer;
   (c) combining the first solution with a second solvent system, wherein the second solvent system is a ($C_3$ to $C_{10}$) ketone, to provide a precipitated block copolymer in a mother liquor;
   (d) adding acetone to the precipitated block copolymer in the mother liquid to provide a mixture of the precipitated block copolymer in the mother liquid and acetone;
   (e) adding a third solvent system to the mixture of the precipitated block copolymer in the mother liquid and acetone, wherein the third solvent system is a non-solvent with respect to at least two types of blocks of the purified block copolymer, to provide a mixture of the precipitated block copolymer in the mother liquid and the mixture of solvents; and
   (f) separating the precipitated block copolymer from the mother liquid and the mixture of solvents to provide a purified block copolymer.

2. The method of claim 1, wherein the third solvent system comprises 2-propanol.

3. The method of claim 1, wherein the second solvent system does not dissolve the polyisobutylene-based block of the block polymer, such that the polyisobutylene-based block precipitates from the mother liquor at about 23° C.

4. The method of claim 1, wherein the method further comprises drying the purified block polymer obtained from Step (f), wherein the drying comprises subjecting the purified block polymer to a reduced atmospheric pressure, to temperature above about 25° C., or both.

5. The method of claim 4, wherein the temperature is about 30° C. to about 60° C.

6. The method of claim 1, wherein the polyisobutylene-based thermoplastic elastomer is suitable for biomedical applications.

7. The method of claim 1, wherein a polystyrene-based end-block of the block polymer comprises polystyrene, wherein the benzene ring moiety of the styrene subunits are individually optionally substituted, or a combination thereof.

8. The method of claim 7, wherein the optionally substituted benzene ring moieties of the styrene subunits comprise one or more polystyrene blocks, poly(4-methylstyrene) blocks, poly(4-methoxystyrene) blocks, poly(4-tert-butylstyrene) blocks, poly(4-(2-hydroxyisopropyl)styrene) blocks, poly(4-(2-methoxyisopropyl)styrene) blocks, poly(3-(2-methoxyisopropyl)styrene) blocks, poly(4-(2-chloroisopropyl)styrene) blocks, poly(4-(2-acetylisopropyl)styrene) blocks, poly(4-(2-acetoxyisopropyl)styrene) blocks, poly(4-chlorostyrene) blocks, poly(4-(epoxyisopropyl)styrene) blocks, or a combination thereof.

9. The method of claim 1, wherein the first solvent system comprises tetrahydrofuran, methylcyclohexane, toluene, benzene, or a combination thereof.

10. The method of claim 1, wherein about 15 to about 25 volumes of the first solvent system is used.

11. The method of claim 1, wherein the block polymer is a copolymer comprising one or more blocks derived from optionally substituted styrene monomers, and one or more blocks derived from isobutylene monomers.

12. The method of claim 1, wherein the second solvent system comprises acetone, methyl ethyl ketone, methyl vinyl ketone, or a combination thereof.

13. The method of claim 1, wherein the first solution and the second solvent system are combined by dropwise addition of the first solution into the second solvent system.

14. The method of claim 1, wherein the third solvent system comprises an alcohol and the third solvent system does not dissolve either the polyisobutylene mid-block or the end blocks of the block polymer.

15. The method of claim 14, wherein the alcohol comprises methanol, ethanol, 1-propanol, 2-propanol, or a $C_4$ alcohol.

16. The method of claim 1, wherein the purified block polymer contains less than about 5 parts per million of any residual monomer.

17. The method of claim 16, wherein the purified block polymer contains less than about 1 part per million of any residual monomer.

18. The method of claim 1, wherein the purified block polymer contains less than about 5 parts per million of styrene monomers, para-methylstyrene monomers, para-methoxystyrene monomers, or any combination thereof.

19. The method of claim 1, wherein an antioxidant is employed in the first solution.

20. The method of claim 19, wherein the antioxidant is a vitamin or an antioxidant suitable for use in biomedical implants.

21. The method of claim 20, wherein the vitamin is vitamin A, vitamin C, or vitamin E.

22. The method of claim 1, wherein an antioxidant is employed in the first solution.

23. The method of claim 1, wherein the separating comprises decanting, draining, or filtering.

24. The method of claim 1, wherein the block polymer is an arborescent copolymer comprising one or more styrene polymeric blocks in combination with one or more isobutylene polymeric blocks.

25. The method of claim 1, wherein the block polymer has thermoplastic elastomeric properties.

26. The method of claim 1, further comprising the step of: applying the purified block polymer to a medical devise.

27. A method for purifying a block polymer comprising the steps of:
   (i) dissolving a block polymer comprising a polyisobutylene-based thermoplastic elastomer having polystyrene-based end blocks in a first solvent system to provide a first solution, wherein the first solvent system comprises one or more solvents, and the solvent system is capable of dissolving a polyisobutylene-based polymer of the thermoplastic elastomer;
   (ii) combining the first solution with a second solvent system, wherein the second solvent system comprises one or more solvents, and the solvent system dissolves a polystyrene-based end block of the block polymer to a greater extent than it dissolves a polyisobutylene-based block of the block polymer, to provide a precipitated block polymer in a mother liquor;

(iii) adding acetone to the mother liquor with precipitated block polymer to provide a mixture of the mother liquor with precipitated block polymer and acetone;

(iv) adding a third solvent system to the mixture of the mother liquor with precipitated block polymer and acetone, wherein the third solvent system is a non-solvent with respect to at least two types of blocks of the precipitated block polymer, to provide a mixture of the precipitated block polymer and the mixture of solvents; and (v) separating the precipitated block polymer from the mixture of solvents to provide a purified block polymer.

28. The method of claim 27, wherein the second solvent system does not dissolve the polyisobutylene-based block of the block polymer, such that the polyisobutylene-based block precipitates from the mother liquor at about 23° C.

29. The method of claim 27, wherein the method further comprises drying the purified block polymer obtained from Step (v), wherein the drying comprises subjecting the purified polymer to a reduced atmospheric pressure, to temperature above about 25° C., or both.

30. The method of claim 29, wherein the temperature is about 30° C. to about 60° C.

31. The method of claim 27, wherein the polyisobutylene-based thermoplastic elastomer is suitable for biomedical applications.

32. The method of claim 27, wherein a polystyrene-based end-block of the block polymer comprises polystyrene, wherein the benzene ring moiety of the styrene subunits are individually optionally substituted, or a combination thereof.

33. The method of claim 32, wherein the optionally substituted benzene ring moieties of the styrene subunits comprise one or more polystyrene blocks, poly(4-methylstyrene) blocks, poly(4-methoxystyrene) blocks, poly(4-tert-butylstyrene) blocks, poly(4-(2-hydroxyisopropyl)styrene) blocks, poly(4-(2-methoxyisopropyl)styrene) blocks, poly(3-(2-methoxyisopropyl)styrene) blocks, poly(4-(2-chloroisopropyl)styrene) blocks, poly(4-(2-acetylisopropyl)styrene) blocks, poly(4-(2-acetoxyisopropyl)styrene) blocks, poly(4-chlorostyrene) blocks, poly(4-(epoxyisopropyl)styrene) blocks, or a combination thereof.

34. The method of claim 27, wherein the first solvent system comprises tetrahydrofuran, methylcyclohexane, toluene, benzene, or a combination thereof.

35. The method of claim 27, wherein about 15 to about 25 volumes of the first solvent system is used in Step (i).

36. The method of claim 27, wherein the second solvent system comprises acetone, methyl ethyl ketone, methyl vinyl ketone, or a combination thereof.

37. The method of claim 27, wherein the first solution and the second solvent system are combined by dropwise addition of the first solution into the second solvent system.

38. The method of claim 27, wherein the purified block polymer contains less than about 5 parts per million of any residual monomer.

39. The method of claim 38, wherein the purified block polymer contains less than about 1 part per million of any residual monomer.

40. The method of claim 27, wherein the purified block polymer contains less than about 5 parts per million of styrene monomers, para-methylstyrene monomers, para-methoxystyrene monomers, or any combination thereof.

41. The method of claim 27, wherein an antioxidant is employed in the first solution.

42. The method of claim 41, wherein the antioxidant is a vitamin or an antioxidant suitable for use in biomedical implants.

43. The method of claim 42, wherein the vitamin is vitamin A, vitamin C, or vitamin E.

44. The method of claim 27, wherein the separating in Step (v) comprises decanting, draining, or filtering.

45. The method of claim 27, wherein the block polymer has thermoplastic elastomeric properties.

46. The method of claim 27, further comprising the step of:
(vi) applying the purified block polymer to a medical devise.

47. A method for purifying a block polymer comprising the steps of:

(A) dissolving about 1 part by weight of a block polymer comprising a polyisobutylene-based thermoplastic elastomer having polystyrene-based end blocks in about 10-30 parts by weight of a first solvent system to provide a first solution, wherein the first solvent system comprises one or more solvents, and the solvent system is capable of dissolving a polyisobutylene-based polymer;

(B) combining the first solution with about 5 to about 10 volumes of a second solvent system, with respect to the volume of the first solution, wherein the second solvent system comprises one or more solvents, and the solvent system dissolves a polystyrene-based end block of the block polymer to a greater extent than it dissolves the internal polyisobutylene-based blocks of the block polymer, to provide a precipitated block polymer in a mother liquor;

(C) adding about 5 to about 10 volumes of acetone, with respect to the volume of the first solution, to the mother liquor with precipitated block polymer to provide a mixture of the mother liquor with precipitated block polymer and acetone;

(D) adding about 1 to about 5 volumes, with respect to the volume of the first solution, of 2-propanol to the mixture of the mother liquor with precipitated block polymer and acetone, to provide a mixture of the precipitated block polymer and the mixture of solvents; optionally followed by adding an additional 1 to about 15 volumes of 2-propanol; and (E) separating the precipitated block polymer from the mixture of solvents to provide a purified block polymer.

48. The method of claim 47, wherein the second solvent system does not dissolve the polyisobutylene-based block of the block polymer, such that the polyisobutylene-based block precipitates from the mother liquor at about 23° C.

49. The method of claim 47, wherein the method further comprises drying the purified block polymer obtained from Step (E), wherein the drying comprises subjecting the purified polymer to a reduced atmospheric pressure, to temperature above about 25° C., or both.

50. The method of claim 49, wherein the temperature is about 30° C. to about 60° C.

51. The method of claim 47, wherein the polyisobutylene-based thermoplastic elastomer is suitable for biomedical applications.

52. The method of claim 47, wherein the purified block polymer contains less than about 5 parts per million of any residual monomer.

53. The method of claim 52, wherein the purified block polymer contains less than about 1 part per million of any residual monomer.

54. The method of claim 47, wherein the purified block polymer contains less than about 5 parts per million of styrene monomers, para-methylstyrene monomers, para-methoxystyrene monomers, or any combination thereof.

55. The method of claim 47, wherein an antioxidant is employed in the first solution.

56. The method of claim 55, wherein the antioxidant is a vitamin or an antioxidant suitable for use in biomedical implants.

57. The method of claim 56, wherein the vitamin is vitamin A, vitamin C, or vitamin E.

58. The method of claim 47, wherein the separating in Step (E) comprises decanting, draining, or filtering.

59. The method of claim 47, wherein the block polymer has thermoplastic elastomeric properties.

60. The method of claim 47, further comprising the step of:
(F) applying the purified block polymer to a medical devise.

* * * * *